(12) United States Patent
Dettmar et al.

(10) Patent No.: US 6,391,294 B1
(45) Date of Patent: May 21, 2002

(54) IN SITU FORMATION OF POLYMERIC MATERIAL

(75) Inventors: Peter William Dettmar; Ian Gordon Jolliffe, both of Hull (GB); Oyvind Skaugrud, Mjoendalen (NO)

(73) Assignee: Reckitt Benckiser Healthcare (UK) Limited, Slough (GB)

( * ) Notice: Subject to any disclaimer, the term of this patent is extended or adjusted under 35 U.S.C. 154(b) by 0 days.

(21) Appl. No.: 09/485,771

(22) PCT Filed: Aug. 10, 1998

(86) PCT No.: PCT/GB98/02410

§ 371 Date: Apr. 12, 2000

§ 102(e) Date: Apr. 12, 2000

(87) PCT Pub. No.: WO99/09962

PCT Pub. Date: Mar. 4, 1999

(30) Foreign Application Priority Data

Aug. 21, 1997 (GB) .............................................. 9717626
Aug. 21, 1997 (GB) .............................................. 9717627

(51) Int. Cl.$^7$ .............................................. A61K 31/74
(52) U.S. Cl. ................................. 424/78.11; 424/78.08; 424/484; 424/486; 424/487; 424/488; 424/400; 514/772; 514/772.1
(58) Field of Search .............................. 424/78.4, 78.17, 424/78.08, 484, 486, 487, 488, 400; 514/772

(56) References Cited

U.S. PATENT DOCUMENTS

| 4,501,835 A | 2/1985 | Berke ........................... 524/32 |
| 4,814,176 A | 3/1989 | Makino et al. .............. 424/457 |
| 4,913,743 A | 4/1990 | Brode et al. ................. 106/162 |
| 4,996,150 A | * 2/1991 | Joung et al. ................ 435/161 |
| 5,456,745 A | 10/1995 | Roreger et al. ............. 106/128 |
| 5,587,175 A | 12/1996 | Viegas et al. ................ 424/427 |
| 6,022,556 A | * 2/2000 | Hardy ......................... 424/443 |

FOREIGN PATENT DOCUMENTS

| EP | 0159604 A2 | 10/1985 | ............ A61K/9/22 |
| EP | 0187703 A2 | 7/1986 | ............ A61K/9/22 |
| EP | 0544529 A1 | 6/1993 | ............ C08B/37/00 |
| GB | 2194144 A | 3/1988 | ............ A61K/9/00 |
| WO | WO92/09636 | 6/1992 | ............ C08B/37/08 |
| WO | WO94/04136 | 3/1994 | ............ A61K/9/58 |
| WO | WO94/06484 | 3/1994 | ............ A61L/15/28 |
| WO | WO96/03973 | 2/1996 | ............ A61K/7/48 |
| WO | WO97/22371 | 6/1997 | ............ A61L/27/00 |

OTHER PUBLICATIONS

WPI Abstract Accession No. 84–143230[23] & JP 590074984 A (Sumitomo) Apr. 27, 1984.
Copy of GB Search Report for GB Application No. 9717627.7 dated Nov. 13, 1997.
Copy of GB Search Report for GB Application No. 9717627.5 dated Nov. 13, 1997.
Copy of GB Search Report for GB Application No. 9817093.9 dated Oct. 29, 1998.
Patent Abstracts of Japan, vol. 006, No. 197, Oct. 6, 1982 7 JP 57 106611 A, Jul. 2, 1982.
Chemical Abstracts, vol. 122, No. 16, Apr. 17, 1995.
Copy of International Search Report for PCT Application No. PCT/GB/02410 dated Dec. 14, 1998.

* cited by examiner

*Primary Examiner*—Thurman K. Page
*Assistant Examiner*—Liliana Di Nola Baron
(74) *Attorney, Agent, or Firm*—Fish & Richardson P.C.

(57) ABSTRACT

A pharmaceutically acceptable bio-adhesive coating, film or gel is formed in situ at a body surface by the reaction of (i) an anionic polymer or tripolyphosphate and (ii) a cationic polymer in the presence of water. The two components are supplied either as separate aqueous solutions or in a single non-aqueous formulation, which can be a liquid suspension tablet, capsule or powder.

15 Claims, No Drawings

IN SITU FORMATION OF POLYMERIC MATERIAL

This invention relates to polymeric material, for example, coatings, films and gels, especially pharmaceutically acceptable bioadhesive coatings, films and gels and more specifically to improved methods for producing such coatings, films and gels.

Many polymers are known to be bioadhesive (i.e. able to adhere to biological surfaces, e.g. mucus, the skin, mucosal surfaces, epithelium etc.) and the value of this property is well recognised. For example, bioadhesives may be used to adhere active agents to specific sites in the body for local drug administration, or to coat particular parts of the body. However, when bioadhesives are applied to such surfaces in aqueous solution they may be easily washed off or mechanically removed, because the strength of adhesion of each individual bioadhesive molecule to the surface is not very high. This may lead to further problems if the bioadhesive materials contain active agents intended for use at one particular site, but which are washed away to other sites.

Thus to improve the retention of bioadhesives at a surface they may be formed into films. Such films may be formed either by chemical crosslinking or by physical interaction of the bioadhesive molecules as they come out of solution. However, all of the known methods of film formation have drawbacks with regard to their use at biological surfaces. For example, if bioadhesive films are formed before being applied to a surface (e.g. by weaving polymer strands or by slow evaporation of aqueous solutions of the polymers) they will be awkward to apply to relatively inaccessible parts of the body (e.g. the back of the throat or the underside of the tongue); furthermore, for a number of biopolymers, much of the bioadhesive character of the films may be lost if they become too dry.

Alternatively, current methods for forming bioadhesive films directly on a surface require the use of volatile solvents, which quickly evaporate to leave a film, but which are not suitable for use on sensitive areas of a body (e.g. open wounds, mucosal surfaces, etc.).

A need exists for coatings, gels and/or films, especially bioadhesive coatings, gels and films, capable of being formed directly on surfaces which avoids the use of volatile solvents.

A further need exists for a formulation which is capable of forming a bioadhesive coating, film or gel in situ and which may be provided to the consumer in stable form in a single dosage form containing both components.

According to the invention there is provided a pharmaceutically acceptable polymeric material formed in situ at a body surface, wherein the material is formed by the reaction of:
i) an anionic polymer or tripolyphosphate (component a); and
ii) a cationic polymer (component b) in the presence of water.

Further according to the invention there is provided a process for the preparation of a pharmaceutically acceptable polymeric material in situ at a body surface by applying
i) an anionic polymer or tripolyphosphate (component a) and;
ii) a cationic polymer (component b)
to the body surface wherein component a) is capable of reacting with component b) to form the polymeric material.

Preferably the polymeric material is a bioadhesive coating, film or gel.

Preferably, the polymers are applied sequentially and the first applied polymer is a bioadhesive polymer.

Preferably component a) has one or more acid (proton donor) groups, for example —COOH and/or —SO$_3$H.

Preferably component b) has one or more basic (proton acceptor) groups, for example —NH$_2$ and/or NHCH$_3$.

Component a) may be selected from any anionic polymers that are water-soluble or dispersible and that will form a coating, gel or film in the presence of component b). Preferred anionic polymers include water-soluble salts of hyaluronic acid, water-soluble salts of alginic acids (e.g. sodium alginate, potassium alginate), water-soluble or dispersible salts of polyacrylic acids (e.g. sodium carbomers), xanthan gum, acacia, pectins, sterculia, carrageenan salts, polylactic acid and water-soluble cellulose derivatives (e.g.sodium carboxymethyl cellulose). Most preferred anionic polymers for use in the present invention are water soluble or dispersible carbomer salts, water-soluble salts of alginic acids and water-soluble salts of cellulose derivatives.

Mixtures of anionic polymers may be used, as long as they do not themselves crosslink to form films until component b) is added to them.

The concentration of component a) in the the bioadhesive coating, gels or films of the invention will depend upon a number of factors (e.g. the strength of the film, gel or coating to be produced, the solubility of the polymers, the required viscosity of the solution etc.). Generally the concentration will preferably be selected from the range 0.1 to 75% weight to volume (w/v), more preferably 0.5 to 25% w/v based on the composition as a whole.

Component b) may be selected from any cationic polymers that are water-soluble or dispersible and that will form a coating, film or gel in the presence of component a). Preferred cationic polymers include water-soluble chitosan salts (e.g. chitosan chloride, chitosan acetate), polylysine, chondroitin salts, diethylaminoethyl dextran and keratin.

Mixtures of component b) may be used to form the bioadhesive films of the invention, as long as they do not interact to form a film themselves until they have been added component a).

The total amount of component b) in the bioadhesive coatings, films or gels of the invention will depend upon a number of factors including the amount of component a) used, the strength of film required, the effectiveness of component b), etc. Generally the concentration will be selected from 0.1 to 75% w/v, more preferably 0.5 to 25% w/v of the composition as a whole.

The preferred amount may be easily determined by simple experimentation, however the total weight ratio of component a) to component b) will generally be from 1:10 to 10:1, more preferably 1:2 to 2:1.

The balance of the coating, film or gel may be water, any other pharmaceutically effective carriers, fillers and/or excipients.

Where component a) is a water-soluble alginate salt, component b) is preferably selected from water-soluble chitosan salts; diethylaminoethyl dextran and chondroitin sulphate; most preferably a water-soluble chitosan salt.

Where component a) is a water-soluble or dispersible carbomer salt, component b) is preferably selected from water-soluble chitosan salts; diethylaminoethyl dextran and chondroitin sulphate; most preferably a water-soluble chitosan salt.

Where component a) is sodium carboxymethyl cellulose, component b) is preferably a water-soluble chitosan salt.

The bioadhesive coatings, films or gels of the invention may optionally further comprise one or more pharmaceutically active agents, for either local or systematic delivery depending upon the site of application of the coating, film or gel.

Suitable active agents for use in such coatings, films or gels of the invention include analgesics, anti-inflammatory agents and antipyretics (e.g. acetaminophen, ibuprofen, naproxen, diclofenac, ketoprofen, choline salicylate, benzydamine, buprenorphine, hydrocortisone, betamethasone); decongestants (e.g. pseudoephedrine, phenylephrine, oxymetazoline, xylometazoline); mineral salts (e.g. zinc gluconate, zinc acetate); cough suppressants (e.g. dextromethorphan, codeine, pholcodine); expectorants (e.g. guaiphenesin, n-acetylcysteine, bromhexine); antiseptics (e.g. triclosan, chloroxylenol, cetylpyridinium chloride, benzalkonium chloride, amylmetacresol, hexylresorcinol, dichlorobenzyl alcohol, benzyl alcohol, dequalinium chloride, silver sulphadiazine); cardiovascular agents (e.g. glyceryl trinitrate); local anaesthetics (e.g. lignocaine, benzocaine); cytoprotectants (e.g. carbenoxolone, sucralfate, bismuth subsalicylate); antiulcer agents (e.g. calcium carbonate, sodium bicarbonate, magnesium trisilicate, magaldrate, cimetidine, ranitidine, nizatidine, famotidine, omeprazole, pantoprazole); antihistamines (e.g. loratidine, terfenadine, diphenhydramine, chlorphenhydramine, triprolidine, acrivastine); antinausea agents (e.g. prochlorperazine, sumatriptan), bowel regulatory agents (e.g. diphenoxylate, loperamide, sennosides); antifungal agents (e.g. clotrimazole); antibiotics (e.g. fusafungine, tyrothricin) and antipsoriasis agents (e.g. dithranol, calcipotriol).

Mixtures of the active agents may be included in the coatings, films or gels of the invention where appropriate.

The active agents may be contained in either of components a) and b) before they are applied to the body surface, but most preferably they are contained in component a).

The concentrations of the active agents will depend upon their standard dosages and whether they are for local or systemic release etc. Generally the suitable concentrations will be readily apparent to one skilled in the art of formulation (normally a concentration range of 0.001 to 10% w/v).

Components a) and b) may optionally contain other suitable excipients depending upon the proposed site of application. Examples of suitable excipients include colours, pH adjusters, flavours, sweeteners, preservatives, suspending agents or plasticisers. The concentrations of such excipients will be readily apparent to one skilled in the art of formulation (although they will normally be used in a concentration range of 0.001 to 10% w/v).

In a first aspect of the present invention components a) and b) are present in aqueous solution.

For the purpose of this invention aqueous solutions of components a) or b) also include aqueous dispersions of said materials.

As hereinbefore described, the aqueous solution of component b) may be applied sequentially in any order or simultaneously with the aqueous solution of component a) but more preferably, the aqueous solution of component b) is applied after the aqueous solution of component a).

The amount of time between the application of the two aqueous solutions may vary depending upon the site of application. For example, where component a) applied first is a biopolymer for use in the throat, the two aqueous solutions should be applied within about 10 seconds of each other. In contrast, on a relatively dry, stable surface such as the arm the aqueous solution which is to be applied second may be applied at any time within 5 minutes of the application of the solution applied initially.

It will be clear that the aqueous solution of component a) and the aqueous solution of component b) must be kept apart until they are combined as they are applied to the body surface.

The aqueous solutions of component a) and component b) may be applied to a surface by any suitable means, depending upon the nature and accessibility of the surface. For example, where the surface is a relatively large area that may be suitably positioned (e.g. the back of a hand, etc.) the solutions may be poured on. The solutions may also be applied by use of a dropper (e.g. an eye dropper); or they may be painted on by use of a brush, although care must be taken not to dip the same brush into the component a) solution and then the component b) solution. Alternatively, the solutions may be dispersed from a double-chambered tube, or a double-barrelled syringe. Where the film is intended to be formed in the oesophagus, the aqueous solutions may be applied by being drunk sequentially.

More preferably, the aqueous solutions of component a) and component b) may be sprayed onto the surface.

Any conventional spraying devices may be used for spraying the individual solutions, for example aerosol sprays, pump sprays or trigger sprays. Most preferably, the spray device will be a pump spray or a trigger spray.

Optionally, the two aqueous solutions may be applied by different means, for example the aqueous solution containing component a) may be painted on and the aqueous solution containing component b) may be sprayed on.

When an aqueous solution of component a) is applied to a surface and an aqueous solution of component b) is applied shortly thereafter (according to a preferred embodiment of this aspect of the invention) only that portion of component a) which comes into contact with component b) will react to form a film. Thus a proportion of component a) (especially that in closest proximity to the surface) may not simply form a film but may be coated by the film formed above it. The film in this case is effectively a coating which can thus encapsulate the unreacted component a) and help to prevent it being removed. Thus the film will coat a reservoir of substantially unreacted component a) in this case. This effect will be most pronounced when the two aqueous solutions are sprayed onto the surface, because the droplets so formed will have the most suitable shape to maximise the encapsulation effect.

In a most preferred embodiment of this aspect of the invention there is provided a process for the preparation of a pharmaceutically acceptable polymeric in situ at a body surface, the polymeric material coating a reservoir of substantially unreacted component a) and holding it in close proximity to the body surface, comprising the steps of applying an aqueous solution of component a) onto the body surface and subsequently applying an aqueous solution of component b) onto the same surface. The method of application is preferably spraying.

Preferably the polymeric material is a bioadhesive coating, film or gel.

In this embodiment, component a) is preferably a bioadhesive polymer, most preferably a water-soluble alginate salt and component b) is most preferably a water-soluble chitosan salt. Optionally, the aqueous solution of component a) also comprises an active agent so that a reservoir containing some of the active ingredient may be formed in close proximity to the surface.

Further according to this first aspect of the present invention, there is provided the use of:
i) an anionic polymer or tripolyphosphate (component a); and
ii) a cationic polymer (component b)
(and optionally one or more active agents) for the preparation of aqueous solutions for application to a body surface to form a pharmaceutically acceptable polymeric material thereon wherein component a) is capable of reacting with component b) to form the material.

Preferably the polymeric material is a bioadhesive coating, film or gel.

Preferably the coating includes a reservoir of substantially unreacted component a).

Optionally, the reservoir of unreacted component a) further comprises one or more active agents such as those exemplified above.

Still further according to this first aspect of the present invention there is provided a pharmaceutical pack comprising:

i) an aqueous solution of an anionic polymer or tripolyphosphate (component a); and
ii) an aqueous solution of a cationic polymer (component b) wherein component a) is capable of reacting with component b) to form a pharmaceutically acceptable polymeric material in situ at a body surface and the pack is suitable for applying the two solutions to the body surface such that the polymeric material is formed at that surface.

Preferably the polymeric material is a bioadhesive coating, film or gel.

The pharmaceutical pack may comprise two discrete containers, one for each aqueous solution; but preferably the pack will comprise two containers which are joined together; or, most preferably, the pharmaceutical pack will comprise a single container having separate compartments for each aqueous solution.

Where the pharmaceutical pack is a single container it may have separate dispensing means for each solution. For example, there may be spray dispensing means fitted at each end of the container (or next to each other) to provide sequential spraying of the two aqueous solutions.

Alternatively, in a preferred embodiment, the pharmaceutical pack comprises a single dispensing means which is most preferably a spray-dispensing means. The dispensing means may be adjusted to either dispense both aqueous solutions simultaneously, or, more preferably, to dispense them sequentially, either by single or multiple activations of the dispensing means.

Still further according to this first aspect of the invention, there is provided the use of a process as described above in therapy, and in particular for the treatment of diseases of the throat and mouth.

Still further according to this first aspect of the invention, there is provided the use of a process as described above for the preparation of a medicament for the treatment of disorders of the upper GI tract.

In a second aspect to the present invention, there is provided a non-aqueous formulation for forming a pharmaceutically acceptable polymeric material in situ at a body surface, the formulation including i) an anionic polymer or tripolyphosphate (component a);
ii) a cationic polymer (component b); and
iii) optionally a pharmaceutically acceptable inert filler or carrier wherein component a) is capable of reacting with component b) to form the polymeric material in situ following application to or ingestion by a mammal.

Preferably the polymeric material is a bioadhesive coating, film or gel.

The formulation may be liquid or solid.

The pharmaceutically acceptable inert filler or carrier of the invention may include a glycol, for example propylene glycol, a medium chain triglyceride oil, for example, Miglyol (RTM) (Huls Chemicals), a glyceride, for example Transcutol (RTM) (Gattefosse) and/or mannitol.

The formulation of this aspect of the present invention may optionally include one or more active agents, for either local or systemic delivery depending upon the site of application of the film. In the case of delivery to the mouth, for example, active agents may be included to provide a local effect such as an analgesic or antiseptic action and/or to provide a systemic effect (for example, an anti-histamine or an anti-nausea agent).

Suitable active agents for use in such films or gels of the invention are as described above.

Mixtures of active agents may be included in the formulation of the invention, where appropriate.

In addition, the formulations of the present invention may optionally contain other suitable excipients depending upon the proposed site and/or mode of application. Examples of suitable excipients are as described above with the inclusion of granulating agents such as polyvinyl pyrrolidone, and/or magnesium stearate.

Preferably, the mammal is a human although it will be appreciated that the present invention can have application in animals.

The present invention thus provides formulations which can be used for preparing pharmaceutically acceptable bioadhesive coatings, gels and films in situ. Unexpectedly, some of the films formed by this process also have improved properties such as strength and adhesion as a result of their targeted delivery.

In one embodiment of this second aspect to the present invention, the formulation is presented as a non-aqueous liquid formulation in which both component a) and component b) are dispersed or suspended.

Such a formulation may be taken orally by drinking or pouring, or by spraying.

Alternatively, in another embodiment of this second aspect to the present invention, the formulation may be in the form of a dry powder which contains components a) and b) (and optionally c)) as an intimate mixture. The powder is suitable for delivery to the mouth or throat via an inhaler. The powder granules, which are of a size of more than 10μm, provide a coating in the mouth or on the throat by absorbing water so that component a) and component b) may react to form a bioadhesive film.

Equally, in another embodiment of this second aspect the formulation may be presented in the form of a tablet or lozenge containing both components necessary to form a bioadhesive film. The tablet or lozenge may be bi-layered, in which case, component a) may be present in one half and component b) may be present in the other half. Alternatively, these components could be presented as an intimate mixture.

On ingestion of the tablet, salivation allows release and dissolution of component a) and component b) so that reaction occurs between them to form a bioadhesive film or a gelatinous mass.

Another embodiment of this second aspect to the present invention relates to a formulation which employs a controlled-release capsule containing both component a) and component b) within a hard or soft capsule. The capsule is made from gelatin or a suitable equivalent and opens in the stomach to allow reaction of components a) and b) to form a bioadhesive film or a gelatinous mass.

The novel formulations of the present invention are all one-component non-aqueous systems containing both component a) and component b). In situ, water which is present at (or which may be provided at) the delivery site is absorbed by the formulation, thereby enabling component a) and component b) to react to form a bioadhesive film or a gel.

It will be appreciated by those skilled in the art that component a) and b) will not crosslink to form a bioadhesive coating, film or gel unless in an aqueous environment. Significant advantages accrue from keeping components a) and b) in a non-aqueous (and therefore non-crosslinking) environment, particularly insofar as the two components may be stored together without reacting therefore allowing simultaneous (and therefore quicker) application to a location in a single dosage form.

Components a) and b) may be applied to the surface by any suitable means, depending upon the nature and accessibility of the surface and on the nature of formulation which is appropriate for delivery to the surface. For example, where the surface is a relatively large area that may be suitably positioned (e.g. an external surface such as the back of a hand, etc.) a liquid formulation may be poured on, or may be applied by use of a dropper (e.g. an eye dropper), or may be painted on by use of a brush, or may be dispersed from a syringe. Where the film is intended to be formed in the oesophagus, the film could be produced by drinking a liquid formulation or by the ingestion of a tablet or capsule formulation. When the film is to be formed on the back of the throat or in the nasal cavity, the dry powder formulation may be the most appropriate to ensure accurate delivery and film formation.

Any conventional spraying devices may be used for spraying the liquid formulation, for example aerosol sprays, pump sprays or trigger sprays.

Most preferably the spray device will be a pump spray or a trigger spray.

Further according to this second aspect of the present invention, there is provided the use of the above formulation in therapy, and in particular for the treatment of diseases of the throat and mouth.

Further according to this aspect of the present invention, there is also provided the use of the above formulation for the preparation of a medicament for the treatment of disorders of the upper GI tract.

The bioadhesive coatings, films or gels according to the invention in this case may act as a barrier to prevent further damage/contamination to wounded areas of skin (e.g. wounds, or sites of eczema etc.), to soothe sore areas of the body (e.g. sore throats etc.); or as systemic drug delivery films (e.g. transdermal films on intact skin, sublingual delivery films on the underside of the tongue etc.). Such coatings, films or gels are particularly useful for local delivery of active agents, as they prevent the active agents from being washed away from the site of application, i.e. they minimise the effect of the active agent on the surrounding tissue (e.g. a topical anaesthetic in the throat).

The bioadhesive coatings, films or gels of the invention may be formed upon any surface of the mammalian body as required. Suitable surfaces include any region of the skin (for example to cover a wound or act as a drug delivery patch), the back of the throat or the oesophagus (e.g. to provide mechanical protection/soothing, or to deliver active agents locally or systematically); the underside of the tongue (as a sublingual dosage form the systemic delivery) or in the nasal cavity, vagina or rectum (as local drug delivery forms).

The invention will now be illustrated by the following Examples.

EXAMPLE 1

| A. Anionic Solution | |
|---|---|
| Sodium alginate (LFR 5/60, Pronova biopolymer) | 2 g |
| Methyl paraben (preservative) | 0.1 g |
| Flavours, sweeteners, colours | q.s. |
| Purified water to | 100 ml |
| B. Cationic Solution | |
| Chitosan chloride (Seacure CL 211, Pronova Biopolymer) | 0.4 g |
| Methyl paraben (preservative) | 0.1 g |
| Flavours, sweeteners, colours | q.s. |
| Purified water to | 100 ml |

Solution A
1. Dissolve the methyl paraben, flavours, sweeteners and colours in the water.
2. Create a vortex in the solution and disperse the chitosan hydrochloride. Stir until dissolved.

Solution B
1. Dissolve the methyl paraben, flavours, sweeteners and colours in the water.
2. Create a vortex in the solution and disperse the sodium alginate. Stir until dissolved.

Between 0.2 and 1 ml of each solution may be sprayed simultaneously onto the back of the throat to form a soothing protective film. This film is of particular benefit to those suffering from a sore throat.

EXAMPLE 2

As Example 1 but the Anionic Solution (A) contains 5% w/v sodium alginate and the Cationic Solution (B) contains 2% w/v chitosan hydrochloride

EXAMPLE 3

As Example 1 but the Anionic Solution (A) also contains 0.66% w/v lignocaine hydrochloride.

A soothing protective film is formed when 0.5 ml of Solution A immediately followed by 0.5 ml of Solution B are sprayed onto the back of the throat. The resulting film also delivers a dose of 3.3 mg of lignocaine hydrochloride providing a local anaesthetic effect.

EXAMPLE 4

| A. Anionic Solution | |
|---|---|
| As Example 1. | |
| B. Cationic Solution | |
| Chitosan chloride (Seacure CL 211, Pronova biopolymer) | 0.4 g |
| Methyl paraben | 0.1 g |
| Benzocaine | 0.2 g |
| Amylmetacresol | 0.16 g |
| Dichlorobenzyl alcohol | 0.24 g |
| Flavours, sweeteners, colours | q.s. |
| Purified water to | 100 ml |

Solution B
1. Dissolve the methyl paraben, flavours, sweeteners and colours in the water.
2. Add the benzocaine, amylmetacresol and dichlorobenzyl alcohol. Stir until dispersed.

3. Create a vortex in the solution and disperse the chitosan chloride. Stir until dissolved.

Spray 0.5 ml of Solution B onto the throat immediately followed by 0.5 ml of Solution A. A soothing protective film having local antibacterial and local anaesthetic properties is formed at the back of the throat.

EXAMPLE 5

As Example 1 but Solution A also comprises 3 g dextromethorphan hydrobromide and 200 mg of menthol BP.

When 0.5 ml of both Solutions A and B are sprayed onto the back of the throat of a patient suffering from a cough a demulcent film is produced providing a local soothing action (due to the menthol) and a systemic cough suppressant effect (due to the dextromethorphan hydrobromide).

EXAMPLE 6

| A. Anionic Solution | |
|---|---|
| Carbomer (Carbopol 974P B. F. Goodrich) | 0.25 g |
| Methyl paraben | 0.1 g |
| Sodium hydroxide | to pH 7 |
| Flavours, sweeteners, colours | q.s. |
| Purified water to | 100 ml |
| B. Cationic Solution | |
| Chitosan chloride (Seacure CL 211, Pronova Biopolymer) | 2 g |
| Methyl paraben | 0.1 g |
| Flavours, Sweeteners, colours | q.s. |
| Purified water to | 100 ml |

Solution A
1. Dissolve the methyl paraben, flavours, sweeteners and colours in the water.
2. Create a vortex in the solution and disperse the carbomer. Stir until well dispersed.
3. Add sodium hydroxide (as a 20% aqueous solution) and stir slowly until homogenous.
4. Check pH is between 6.5 and 7.5 and adjust volume.

Solution B
1. Dissolve the methyl paraben, flavours, sweeteners and colours in the water.
2. Create a vortex in the solution and disperse the chitosan chloride. Stir until dissolved.

When between 0.2 ml and 1 ml of both Solutions A and B are sprayed simultaneously onto the back of the throat of a sore throat sufferer a soothing protective film is formed.

EXAMPLE 7

As Example 6 but Solution A also contains 0.16 g amylmetacresol and 0.24 g dichlorobenzyl alcohol.

EXAMPLE 8

As Example 6 but Solution A also contains 1.6 g calcium carbonate and 2.6 g sodium bicarbonate.

When a 5 ml spoonful of Solution A is swallowed, followed after 10 to 30 seconds by a 5 ml spoonful of Solution B, a protective film is formed in the oesophagus which has neutralisation capacity to protect against gastric reflux.

EXAMPLE 9

| A. Anionic Solution | |
|---|---|
| Sodium alginate (LFR 5/60, Pronova Biopolymer) | 5 g |
| Methyl paraben | 0.1 g |
| Flavours, sweeteners, colours | q.s. |
| Purified water to | 100 ml |
| B. Cationic Solution | |
| Chitosan hydrochloride (Seacure CL 211, Pronova biopolymer) | 1 g |
| Methyl paraben | 0.1 g |
| Flavours, sweeteners, colours | q.s. |
| Purified water to | 100 ml |

Solution A
1. Dissolve the methyl paraben, flavours, sweeteners and colours in the water.
2. Create a vortex in the solution and disperse the sodium alginate. Stir until dissolved.

Solution B
1. Dissolve the methyl paraben, flavours, sweeteners and colours in the water.
2. Create a vortex in the solution and disperse the chitosan chloride. Stir until dissolved.

When 0.2 to 1 ml of each solution are sprayed simultaneously onto the back of the throat a soothing protective film is formed.

EXAMPLE 10

As Example 1 but Solution A also contains 216 mg of buprenorphine hydrochloride.

When 0.1 ml of Solution A, followed immediately by 0.1 ml of Solution B, are sprayed onto the underside of the tongue a film is formed providing systemic (sublingual) delivery of buprenorphine hydrochloride.

EXAMPLE 11

As Example 1 but Solution A also contains 10 g povidone iodine complex.

When 5 ml of Solution A, immediately followed by 5 ml of Solution B, are sprayed onto a skin wound a protective/disinfecting film is formed.

EXAMPLE 12

| A. Anionic Solution | |
|---|---|
| Amidated low methoxy Pectin | 6 g |
| Methyl paraben (preservative) | 0.1 g |
| Flavours, sweeteners, colours | q.s. |
| Purified water to | 100 ml |
| B. Cationic Solution | |
| Chitosan chloride (Seacure CL 211, Pronova Biopolymer) | 0.4 g |
| Methyl paraben (preservative) | 0.1 g |
| Flavours, sweeteners, colours | q.s. |
| Purified water to | 100 ml |

Solution A
1. Dissolve the methyl paraben, flavours, sweeteners and colours in the water.
2. Create a vortex in the solution and disperse the amidated pectin. Stir until dissolved.

Solution B
1. Dissolve the methyl paraben, flavours, sweeteners and colours in the water.
2. Create a vortex in the solution and disperse the chitosan hydrochloride. Stir until dissolved.

Between 0.2 and 1 ml of each solution may be sprayed simultaneously onto the back of the throat to form a soothing protective film. This film is of particular benefit to those suffering from a sore throat.

EXAMPLE 13

As Example 12 but the Anionic Solution (A) contains 10% pectin and the Cationic Solution (B) contains 2% w/v chitosan hydrochloride.

EXAMPLE 14

As Example 12 but the Cationic Solution (B) also contains 0.66% w/v lignocaine hydrochloride.

When 0.5 ml of Solution B immediately followed by 0.5 ml of Solution A are sprayed onto the back of the throat a soothing protective film is formed, which also delivers a dose of 3.3 mg of lignocaine hydrochloride providing a local anaesthetic effect.

EXAMPLE 15

A. Anionic Solution

As Example 12.
B. Cationic Solution

| | |
|---|---|
| Chitosan chloride (Seacure CL 211, Pronova biopolymer) | 0.4 g |
| Methyl paraben | 0.1 g |
| Benzocaine | 0.2 g |
| Amylmetacresol | 0.16 g |
| Dichlorobenzyl alcohol | 0.24 g |
| Flavours, sweeteners, colours | q.s. |
| Purified water to | 100 ml |

Solution B
1. Dissolve the methyl paraben, flavours, sweeteners and colours in the water.
2. Add the benzocaine, amylmetacresol and dichlorobenzyl alcohol. Stir until dispersed.
3. Create a vortex in the solution and disperse the chitosan chloride. Stir until dissolved.

Spray 0.5 ml of Solution B onto the throat immediately followed by 0.5 ml of Solution A. A soothing protective film having local antibacterial and local anaesthetic properties is formed at the back of the throat.

EXAMPLE 16

A. Anionic Solution

| | |
|---|---|
| Low methoxy amidated pectin | 6 g |
| Methyl paraben | 0.1 g |
| Flavours, sweeteners, colours | q.s. |
| Purified water to | 100 ml |

B. Cationic Solution

| | |
|---|---|
| Chitosan hydrochloride (Seacure CL 211, Pronova biopolymer) | 1 g |
| Methyl paraben | 0.1 g |
| Flavours, sweeteners, colours | q.s. |
| Purified water to | 100 ml |

Solution A
1. Dissolve the methyl paraben, flavours, sweeteners and colours in the water.
2. Create a vortex in the solution and disperse the pectin. Stir until dissolved.

Solution B
1. Dissolve the methyl paraben, flavours, sweeteners and colours in the water.
2. Create a vortex in the solution and disperse the chitosan chloride. Stir until dissolved.

When 0.2 to 1 ml of each solution are sprayed simultaneously onto the back of the throat a soothing protective film is formed.

EXAMPLE 17

| | |
|---|---|
| Chitosan chloride (Seacure CL211, Pronova Biopolymer a.s.) | 2 g |
| Sodium alginate (LFR5/60, Pronova Biopolymer a.s.) | 10 g |
| Flavours, sweeteners colours and preservatives | q.s. |
| Propylene glycol to | 100 g |

The sodium alginate and chitosan chloride powders are dispersed in propylene glycol. The remaining ingredients are then added and mixed until dispersed to form a sprayable liquid formulation. The formulation is filled into a suitable spray pack and between 0.2 and 1.0 ml of the suspension is sprayed onto the back of the throat to provide a soothing protective film. This formulation is of particular benefit to sore throat sufferers.

EXAMPLE 18

A formulation identical to that of Example 17 but including 0.66% lignocaine hydrochloride was prepared. 0.5 ml of a solution of the formulation was sprayed onto the back of the throat to provide a soothing protective film. The film also delivered a dose of 3.3 mg of lignocaine hydrochloride to provide a local anaesthetic effect.

EXAMPLE 19

A formulation identical to the formulation of Example 18 but further including Benzocaine 0.2 g, Amylometacresol 0.16 g, and Dichlorobenzyl alcohol 0.24 g was prepared in the manner described in Example 17. 0.5 ml of a solution of the formulation was sprayed onto the back of the throat to provide a soothing protective film which also delivered a dose of local anaesthetic and an anti-bacterial agent. This formulation provided a treatment for sore throats.

EXAMPLE 20

The formulation of Example 20 is identical to the formulation of Example 19, except that the propylene glycol base was replaced by a medium chain triglyceride oil (Miglyol, Huls Chemicals).

EXAMPLE 21

The formulation of Example 21 is identical with the formulation of Example 19, except that the propylene glycol base is replaced by Transcutol (a glyceride-based liquid from Gattefosse).

EXAMPLE 22

| Carbomer (Carbopol 974P, B. F. Goodrich) | 0.25 g |
| Chitosan chloride (Seacure CL211, Pronova Biopolymer a.s.) | 2 g |
| Flavours, sweeteners colours and preservatives | q.s. |
| Medium chain triglyceride oil (Miglyol 812) | 100 g |

The chitosan chloride powders are dispersed in propylene glycol. The remaining ingredients are then added and mixed until dispersed. The resulting dispersion is filled into a suitable spray pack. Between 0.2 and 1.0 ml of the suspension was sprayed onto the back of the throat to provide a soothing protective film. The film soothes sore throats. Further examples of non-aqueous liquid-bases which may be used alone or in combination are: Polyethylene glycol 200 to 400, evening primrose oil, neem tree oil, vegetable oils such as arachis oil and tea tree oil.

Example 23

| Chitosan chloride (Seacure CL211, Pronova Biopolymer a.s.) | 8 mg |
| Sodium alginate (LFR5/60, Pronova Biopolymer a.s.) | 17 mg |
| Triclosan | 25 mg |
| Lecithin | 5 mg |
| Colloidal silicon dioxide | 4.5 mg |
| Medium chain triglyceride oil | 500 mg |

The ingredients were mixed together and filled into a hard gelatin capsule shell using conventional liquid filling equipment for liquid filling hard gelatin capsules. The capsule was dispersed in 0.1M hydrochloric acid at 37° C. in order to simulate gastric conditions. The capsule ruptures and the contents gel to form a matrix due to the interaction of the polymers. The bulk of the gelled matrix remains intact for over 12 hours, slowly releasing the triclosan by diffusion and erosion processes. On ingestion, the capsule provided slow release of the drug into the stomach to provide a continued concentration of triclosan in the stomach for several hours; this provided an effective treatment of H. Pylori infections.

EXAMPLE 24

| Chitosan chloride (Seacure CL211, Pronova Biopolymer a.s.) | 8 mg |
| Sodium alginate (LFR5/60, Pronova Biopolymer a.s.) | 17 mg |
| Pseudoephedrine Hydrochloride | 120 mg |
| Lecithin | 5 mg |
| Colloidal silicon dioxide | 4.5 mg |
| Medium chain triglyceride oil | 500 mg |

The ingredients were mixed together and filled into a hard gelatin capsule shell using conventional liquid filling equipment for liquid filling hard gelatin capsules. The resulting capsule provides a slow release of water soluble drug over the period of 12 hours, with the advantage of reducing the required dosing frequency as compared with standard dosage forms such as tablets.

EXAMPLE 25

| Chitosan chloride (Seacure CL211, Pronova Biopolymer a.s.) | 10 mg |
| Sodium alginate (LFR5/60, Pronova Biopolymer a.s.) | 30 mg |
| Triclosan | 25 mg |
| Gelucire 53/60 (Gattefosse) | 300 mg |

The Gelucire 53/60 was melted and the remaining ingredients were added to the melt and dispersed. The resulting mixture was filled into hard gelatin capsules and allowed to set. On ingestion, the capsule slowly released the contents from the waxy matrix which had gelled at the surface due to the interaction of the polymers.

EXAMPLE 26

| Chitosan chloride (Seacure CL211, Pronova Biopolymer a.s.) | 28.0% |
| Sodium alginate (LFR5/60, Pronova Biopolymer a.s.) | 71.0% |
| Polyvinyl pyrrolidone (Povidone 30 (Kollidon 30 BASF)) | 1.0% |
| Flavours, sweeteners and colour | q.s. |

The Povidone was dissolved in ethanol to form a 2% solution suitable for granulating. The chitosan and the sodium alginate were mixed in dry form and a suitable amount of the granulating solution was added to form a wet mass. The wet mass was pushed through a 500 µm screen and the screened wet mass was dried at 25° C. overnight to remove the ethanol. The resulting dry granules were passed through a 150 µm screen and fine particles were sieved off through a 53 µm screen. The resulting granules were collected and filled into a size 2 capsule shell without compacting. The capsules were put into a Spinhaler (TM of Fisons) device and the device was primed to rupture the capsule so as to provide a dry powder for inhalation. The inhaled powder coated the inside of the mouth and throat and provided a soothing coating which protected against further mechanical irritation in the case of sore throats, sore mouths and ulcers.

EXAMPLE 27

The formulation of Example 27 is identical with the formulation of Example 26, except that the formulation of Example 27 also included benzocaine hydrochloride. The benzocaine hydrochloride was added to the granules in such an amount that each 40 mg of granules contained 10mg of benzocaine hydrochloride. The formulation was coated inside the mouth in the same manner as in Example 10 and provided local anaesthetic pain relief in addition to the soothing and protecting effects described above.

EXAMPLE 28

A bilayer tablet was formed using the following ingredients:

| Layer one: | |
|---|---|
| Sodium alginate (LFR 5/60, Pronova Biopolymer a.s.) | 125 mg |
| Polyvinyl pyrrolidone (Povidone 30 (Kollidon 30 BASF)) | 25 mg |
| Mannitol | 350 mg |
| Flavours and sweeteners | q.s. |
| Magnesium stearate | 15 mg |
| Layer two: | |
| Chitosan chloride (Seacure CL211, Pronova Biopolymer a.s.) | 50 mg |
| Polyvinyl pyrrolidone (Povidone 30 (Kollidon 30 BASF)) | 25 mg |
| Mannitol | 425 mg |
| Flavours and sweeteners | q.s. |
| Magnesium stearate | 15 mg |

Each layer was separately prepared in the same manner. For each layer, all the ingredients except the flavour and the magnesium stearate were mixed in a high-speed mixer granulator. The mixture was granulated by adding isopropanol (200 mls per Kg) and the granulated mixture was subsequently dried at 50° C. in a fluid bed dryer. The dried granules were sieved after which the flavour and magnesium stearate were added and mixed with the granules so as to give the final tablet mix for each layer. The two separate layers were then pressed into tablets on a bilayer press. When the tablets were sucked, they slowly released polymer from each side which then interacted with each other to form a film on the surface of the mouth and throat. The resulting film provided relief for sufferers of dry mouth and sore throats.

EXAMPLE 29

The formulation of Example 29 is identical to the formulation of Example 28, except that the formulation included calcium carbonate (100 mg) and magnesium trisilicate (100 mg) in each layer. On sucking the bilayer tablets, the polymers interacted to form a neutralising coating in the oesophagus which protected against acid reflux.

EXAMPLE 30

| Layer one: | |
|---|---|
| Carbomer (Carbopol 974P, B F Goodrich) | 80 mg |
| Sodium bicarbonate | 15 mg |
| Polyvinyl pyrrolidone (Providone 30 (Kollidon 30 BASF)) | 25 mg |
| Mannitol | 350 mg |
| Flavours and sweeteners | q.s. |
| Magnesium stearate | 15 mg |
| Layer two: | |
| Chitosan chloride (Seacure CL211, pronova Biopolymer a.s.) | 50 mg |
| Polyvinyl pyrrolidone (Providone 30 (Kollidon 30 BASF) | 25 mg |
| Mannitol | 425 mg |
| Flavours and sweeteners | q.s. |
| Magnesium stearate | 15 mg |
| Lignocaine hydrochloride | 3.3 mg |

The bilayer tablet was prepared in the same manner as for Example 28. When sucked, the bilayer tablet provided a local anaesthetic to the mouth and throat which relieved the pain of ulcers and sore throats. The polymers reacted to give a soothing protective film which additionally held the local anaesthetic in place so as to give a longer duration of action.

Further active ingredients which are suitable for incorporation in a sustained release formulation such as those exemplified above include:
Pseudoephedrine hydrochloride
Dextromethorphan hydrobromide
Diclofenac sodium
Ketoprofen
Theophylline hydrobromide
Sodium cromoglycate
Ketoconazole
Isosorbide dinitrate

What is claimed is:

1. A non-aqueous liquid formulation for forming a pharmaceutically acceptable polymeric material in situ at a body surface, the formulation comprising:
   (i) a water soluble salt of alginic acid or a water-soluble or water-dispersible salt of a polyacrylic acid (component (a));
   (ii) a cationic polymer (component (b)); and
   (iii) a pharmaceutically acceptable inert filler or carrier selected from the group consisting of glycols, medium chain triglycerides, glycerides, evening primrose oil, neem tree oil and vegetable oils,
   wherein component (a) is capable of reacting with component (b) to form the pharmaceutically acceptable polymeric material in situ at a body surface following application to or ingestion by a mammal.

2. A formulation according to claim 1 wherein the polymeric material is a bioadhesive coating, a film or gel.

3. A formulation according to claim 1 wherein the concentration of component (a) in the polymeric material is from 0.1 to 75% weight per volume (w/v).

4. A formulation according to claim 3 wherein the concentration of component (a) in the polymeric material is from 0.5 to 25% w/v.

5. A formulation according to claim 1 wherein component (b) is selected from the group consisting of water-soluble chitosan salts, polylysine, chondroitin salts, diethylaminoethyl dextran, and keratin.

6. A formulation according to claim 5 wherein the concentration of component (b) in the polymeric material is from 0.1 to 75% weight per volume (w/v).

7. A formulation according to claim 6 wherein the concentration of component (b) in the polymeric material is from 0.5 to 25% w/v.

8. A formulation according to claim 2 in which the weight ratio of component (a) to component (b) ranges from 1:10 to 10:1.

9. A formulation, according to claim 8 in which the weight ratio ranges from 1:2 to 2:1.

10. A formulation according to claim 2 in which component (a) is a water-soluble alginate salt and component (b) is a water-soluble chitosan salt, dimethylaminoethyl dextran or chondroitin sulfate.

11. A formulation according to claim 10 in which component (b) is a water-soluble chitosan salt.

12. A formulation according to claim 2 in which component (a) is a water-soluble or water-dispersible salt of a polyacrylic acid and component (b) is a water-soluble chitosan salt, dimethylaminoethyl dextran or chondroitin sulfate.

13. A formulation according to claim 12 in which component (b) is a water-soluble chitosan salt.

14. A formulation according to claim 1 wherein the polymeric material further comprises one or more active agents selected from the group consisting of: acetaminophen, ibuprofen, naproxen, diclofenac, ketoprofen, choline salicylate, benzydamine, buprenorphine, hydrocortisone, betamethasone, pseudoephedrine, phenylephrine, oxymetazoline, xylometazoline, zinc gluconate, zinc acetate, dextromethorphan, codeine, pholcodine, guaiphenesin, N-acetylcysteine, bromhexine; triclosan, chloroxylenol, cetylpyridinium chloride, benzalkonium chloride, amylmetacresol, hexylresorcinols, dichlorobenzyl alcohol, benzyl alcohol, dequalinium chloride, silver sulphadiazine, glyceryl trinitrate, lignocaine, benzocaine, carbenoxolone, sucralfate, bismuth subsalicylate, calcium carbonate, sodium bicarbonate, magnesium trisilicate, magaldrate, cimetidine, ranitidine, nizatidine, famotidine, omeprazole, pantoprazole, loratidine, terfenadine, diphenhydramine, chlorphenhydramine, triprolidine, acrivastine, prochlorperazine, sumatriptan, diphenoxylate, loperamide, sennosides, clotrimazole, fusafungine, tyrothricin, dithranol, calcipotriol, and pharmaceutically acceptable mixtures thereof.

15. A formulation according to claim 14 in which the active agent is contained in component (a).

* * * * *